(12) United States Patent
Yamada et al.

(10) Patent No.: US 7,268,257 B1
(45) Date of Patent: Sep. 11, 2007

(54) PROCESS FOR PRODUCING TOLTERODINE

(75) Inventors: Tsukusa Yamada, Ashiya (JP); Nobushige Itaya, Nishinomiya (JP); Masahide Tanaka, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/421,192

(22) Filed: May 31, 2006

(51) Int. Cl.
C09B 11/02 (2006.01)
(52) U.S. Cl. .................................... 564/316; 564/315
(58) Field of Classification Search ................ None
See application file for complete search history.

(56) References Cited

U.S. PATENT DOCUMENTS

| | | | |
|---|---|---|---|
| 5,382,600 A | 1/1995 | Jönsson et al. | |
| 5,922,914 A | 7/1999 | Gage et al. | |
| 6,822,119 B1 | 11/2004 | Kumar et al. | |

OTHER PUBLICATIONS

Chen, G., et al., "Rhodium-Catalyzed Asymmetric 1,4-Addition of Arylboronic Acids to Coumarins: Asymmetric Synthesis of (R)-Tolterodine", Org. Lett., vol. 7, No. 11, pp. 2285-2288 (2005).
Kennedy-Smith, J. J., et al., "Rhenium-Catalyzed Aromatic Propargylation", Org. Lett., vol. 6, No. 8, pp. 1325-1327 (2004).
Srinivas, K., et al., "An Improved, Scalable, and Impurity-Free Process for Tolterodine Tartrate", Org. Proc. Res. & Develop., vol. 9, No. 3, pp. 314-318 (2005).
Botteghi, C., et al., "A New Efficient Route to Tolterodine", Org. Proc. Res. & Develop., vol. 6, pp. 3719-383 (2002).
Andersson, P. G., et al., "Asymmetric Total Synthesis of (+)-Tolterodine, a New Muscarinic Receptor Antagonist, via Copper-Assisted Asymmetric Conjugate Addition of Aryl Grignard Reagents to 3-Phenyl-prop-2-enoyl-oxazolidinones", J. Org. Chem., vol. 63, pp. 8067-8070 (1998).

*Primary Examiner*—Samuel Barts
(74) *Attorney, Agent, or Firm*—Foley and Lardner LLP

(57) ABSTRACT

The present invention provides a process for producing tolterodine of the formula (1) or its salt, which comprises a step reacting a compound of the formula (2) with a base to obtain a reaction product; a step reacting the reaction product with a compound of the formula (3) to obtain a compound of the formula (4); and a step eliminating the protective group from the compound of the formula (4), and also provides a process for producing the compound of the formula (3).

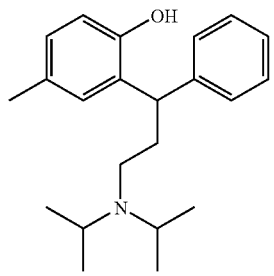

(1)

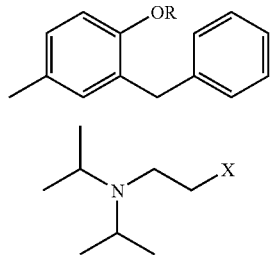

(2)

(3)

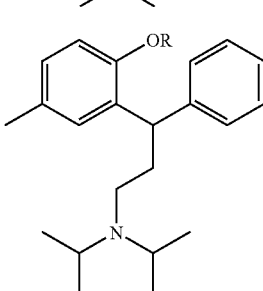

(4)

21 Claims, No Drawings

PROCESS FOR PRODUCING TOLTERODINE

BACKGROUND OF THE INVENTION

Field of the Invention

The present invention relates to a process for producing tolterodine useful as a therapeutic agent for urinary incontinence and its intermediate.

As a process for producing tolterodine, the process shown in Scheme 1 below is known (for example, WO98/29402). This method involves ring opening and methylation of the lactone derivative obtained from the reaction of cinnamic acid and p-cresol, followed by reduction of the ester, tosylation, diisopropylamination and demethylation to obtain tolterodine.

The process above is not an economical one because it has many steps to obtain. A similar process (WO89/06644) is known, but also has many steps, it is not an economical process for producing tolterodine.

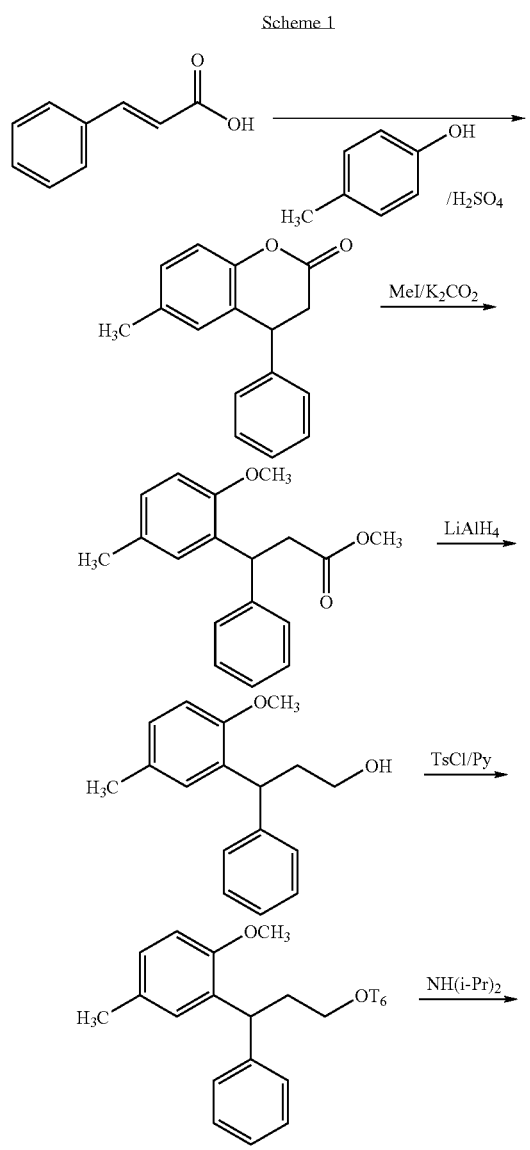

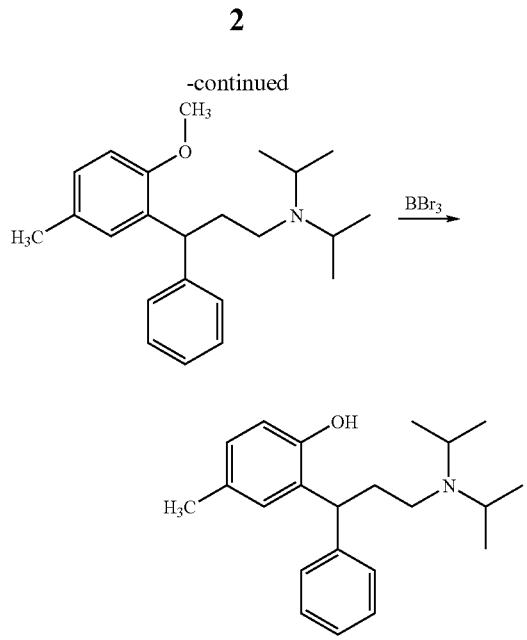

As shown in Scheme 2, it is also known that lactone derivative obtained from the reaction of cinnamic acid and p-cresol is reduced to lactol derivative and then reducing the lactol derivative in the presence of the diisopropylamine (WO03/014060). This method advantageously reduces the number of steps, but the reduction in the process needs to be carried out under hydrogen pressure condition of 10 atmospheres, and the process is not necessarily an easy process for industrial preparation.

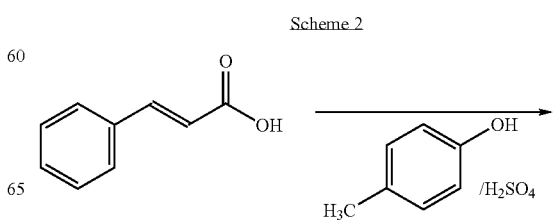

-continued

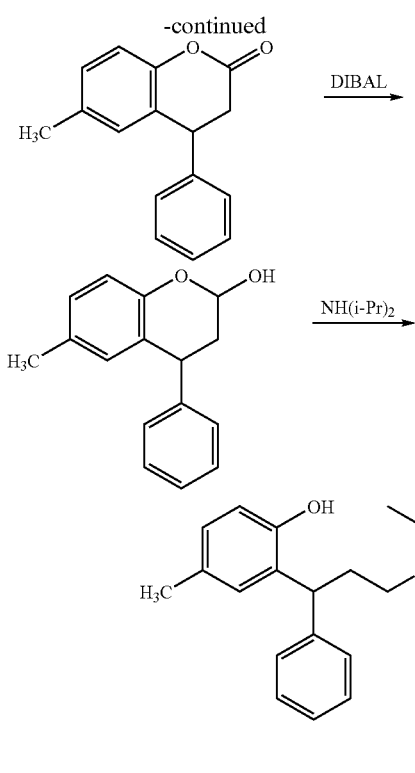

SUMMARY OF THE INVENTION

An object of the present invention is to provide an industrially and economically advantageous process for producing tolterodine or its intermediate in a smaller number of steps.

This and other objects of the present invention will be apparent from the following description.

The present invention relates to the followings:

<1> A process for producing tolterodine of the formula (1) or its salt;

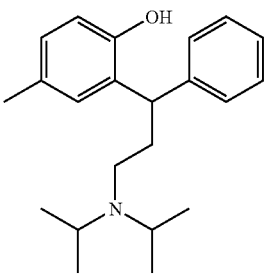 (1)

which comprises a step reacting a compound of the formula (2)

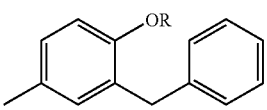 (2)

wherein R represents a protective group of phenol group, with a base to obtain a reaction product, (hereinafter the step may be referred to as Step 1), a step reacting the reaction product with a compound of the formula (3)

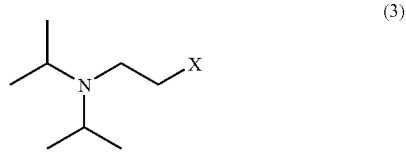 (3)

wherein X represents halogen atom, alkylsulfonyloxy group or arylsulfonyloxy group, to obtain a compound of the formula (4)

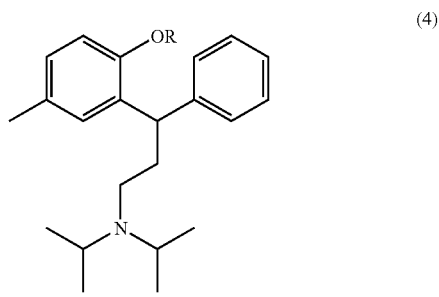 (4)

wherein R has the same meaning as defined above (hereinafter the step may be referred to as Step 2), and a step eliminating the protective group from the compound of the formula (4) (hereinafter the step may be referred to as Step 3).

<2> The process according to <1>, wherein the base is alkyl metal, metal dialkylamide or metal hydride.

<3> The process according to <2>, wherein the base is alkyl lithium or lithium dialkylamide.

<4> The process according to <3>, wherein the base is n-butyllithium, sec-butyllithium, tert-butyllithium or lithium diisopropylamide.

<5> The process according to <4>, wherein the base is n-butyllithium or sec-butyllithium.

<6> The process according to any of <1> to <5>, wherein X in the compound of the formula (3) is chlorine atom, bromine atom, methanesulfonyloxy group, toluenesulfonyloxy group or benzenesulfonyloxy group.

<7> The process according to <6>, wherein X in the compound of the formula (3) is chlorine atom.

<8> The process according to any <1> to <7>, wherein R is alkyl group having 1 to 6 carbon atoms, benzyl group optionally substituted, trialkylsilyl group having 3 to 18 carbon atoms or 2-tetrahydropyranyl group.

<9> The process according to <8>, wherein R is methyl group, benzyl group, trimethylsilyl group, di-tert-butylmethylsilyl group, tert-butyldimethylsilyl group or 2-tetrahydropyranyl group.

<10> The process according to any of <1> to <9>, wherein the elimination of the protective group from the compound of the formula (4) is carried out by contacting the compound (4) with deblocking agent.

<11> The process according to <10>, wherein R is alkyl group having 1 to 6 carbon atoms or benzyl group optionally substituted and the deblocking agent is hydrobromic acid or boron tribromide, R is trialkylsilyl group having 3 to 18 carbon atoms and the deblocking agent is fluoride or mineral acid; or R is 2-tetrahydropyranyl group and the deblocking agent is mineral acid.

<12> The process according to any of any of <1> to <9>, wherein R is benzyl group optionally substituted and the elimination of R is carried out by hydrogenation of the compound of the formula (4) in the presence of reduction catalyst.

<13> A process for producing a compound of the formula (4)

which comprises a step reacting a compound of the formula (2) with a base to obtain a reaction product, and a step reacting the reaction product with a compound of the formula (3).

<14> The process according to <13>, wherein the base is alkyl metal, metal dialkylamide or metal hydride.

<15> The process according to <14>, wherein the base is alkyl lithium or lithium dialkylamide.

<16> The process according to <15>, wherein the base is n-butyllithium, sec-butyllithium, tert-butyllithium or lithium diisopropylamide.

<17> The process according to <16>, wherein the base is n-butyllithium or sec-butyllithium.

<18> The process according to any of <13> to <17>, wherein X in the compound of the formula (3) is chlorine atom, bromine atom, methanesulfonyloxy group, toluenesulfonyloxy group or benzenesulfonyloxy group.

<19> The process according to <18>, wherein X in the compound of the formula (3) is chlorine atom.

<20> The process according to any of <13> to <19>, wherein R is alkyl group having 1 to 6 carbon atoms, benzyl group optionally substituted, trialkylsilyl group having 3 to 18 carbon atoms or 2-tetrahydropyranyl group.

<21> The process according to <20>, wherein R is methyl group, benzyl group, trimethylsilyl group, di-tert-butylmethylsilyl group, tert-butyldimethylsilyl group or 2-tetrahydropyranyl group.

Hereinafter, the tolterodine of the formula (1), the compounds of the formula (2), the compound of the formula (3) and the compounds of the formula (4) may be referred to as the compound (1), the compound (2), the compound (3) and the compound (4), respectively.

DESCRIPTION OF PREFERRED EMBODIMENTS

The compound (2) can be manufactured according to the scheme given below with a reference to the method described in WO98/29402.

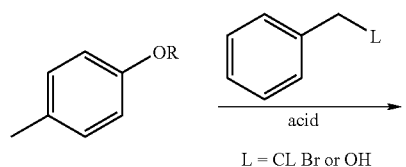

L = CL Br or OH

-continued

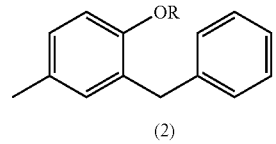

(2)

Examples of R include alkyl group having 1 to 6 carbon atoms, benzyl group optionally substituted, trialkylsilyl group having 3 to 18 carbon atoms, 2-tetrahydropyranyl group, and the like.

Examples of the alkyl group having 1 to 6 carbon atoms include methyl group, ethyl group, n-propyl group, isopropyl group, n-butyl group, isobutyl group, tert-butyl group, sec-butyl group, n-pentyl group, isopentyl group, neopentyl group, n-hexyl group, isohexyl group, and the like. Methyl group is preferred in view of its reactivity and economics.

Examples of the benzyl group optionally substituted include benzyl group, (C1-4alkoxy)benzyl group (e.g. 4-methoxybenzyl group, etc.), nitrobenzyl group (e.g. 4-nitrobenzyl group, etc.), and the like. Benzyl group is preferred in view of its reactivity and economics.

Examples of the trialkylsilyl group having 3 to 18 carbon atoms include trimethylsilyl group, di-tert-butylmethylsilyl group, tert-butyldimethylsilyl group, and the like.

Examples of X in the formula (3) include halogen atom and methanesulfonyloxy group, toluenesulfonyloxy group or benzenesulfonyloxy group. Examples of halogen atom include chlorine, bromine, and the like, and chlorine atom is preferred in view of the cost and reactivity.

Step 1

Step 1 is a step for obtaining the reaction product by reacting the compound (2) with a base. The reaction is carried out by mixing the compound (2) and a base. The mixing is preferably carried out by adding a base to the solution of the compound (2) in a solvent, or by adding the solution of the compound (2) in a solvent to the solution of a base in a solvent.

The base used is a strong base, and examples thereof include alkyl metals, metal dialkylamides, metal hydrides, and the like. Examples of the alkyl metals include alkyl-lithium (e.g. n-butyllithium, sec-butyllithium, tert-butyl-lithium, etc.), and the like. Examples of the matal dialkylamides include bromomagnesium dialkylamide (e.g. boromomagnesium diethylamide, bromomagnesium diisopropylamide, etc.), lithium dialkylamide (e.g. lithium diisopropylamide, etc.), and the like. Examples of the metal hydrides includes sodium hydride, potassium hydride, and the like. N-butyllithium and sec-butyllithium are preferred in view of the safety and economics.

The amount of the base is generally 1 to 2 mols, preferably 1.2 to 1.8 mols per 1 mol of the compound (2) in view of the yield and the effect corresponding to the amount.

Examples of the solvent used include at least one kind of ether solvent such as diethyl ether, tetrahydrofuran, dimethoxyethane, diethoxymethane, dioxane, tert-butyl methyl ether, cyclopentyl methyl ether and the like, a mixture of the ether solvent and hydrocarbon solvent such as toluene, xylene, heptane, hexane, and the like. When the mixture of the ether solvent and hydrocarbon solvent is used, the ratio of the ether solvent in the mixture is preferably 2% by weight or more, more preferably 4% by weight or more. The amount of the solvent used is generally 0.5 to 10 liters, preferably 0.5 to 7 liters per 1 mol of the compound (2) in view of the mixing efficiency and the reaction speed.

The reaction temperature is generally in the range from −100 to 20° C., preferably from −80 to 10° C. in view of the reaction speed, industrial operation and prevention of formation of by-product.

The reaction time depends on the reaction temperature, and is generally 2 and 10 hours.

The reaction product in the form of the reaction mixture obtained in Step 1 is usually subjected to the following Step 2 without purification.

Step 2

Step 2 is a step for obtaining the compound (4) by reacting the reaction mixture obtained in Step 1 with the compound (3). As the reaction product obtained in Step 1 is subjected to Step 2 in the form of the reaction mixture, the reaction in Step 2 is usually carried out by adding the compound (3) to the reaction product contained in the reaction mixture obtained in Step 1.

The amount of the compound (3) is usually 1 to 2 mols, preferably 1.2 to 1.8 mols per 1 mol of the compound (2) in view of the yield and the effect corresponding to the amount.

The same solvent as in Step 1 can be used and usually, the solvent contained in the reaction mixture obtained in Step 1 can be used as it is. The amount of the solvent is generally 0.5 to 10 liters, preferably 0.5 to 7 liters, which include the amount brought form Step 1, per 1 mol of the compound (2).

The reaction temperature is generally in the range from −100 to 20° C., preferably from −80 to 10° C. in view of the reaction speed, industrial operation and prevention of formation of by-product.

The reaction time depends on the reaction temperature, and is generally 1 to 5 hours.

After the reaction, water is added to the reaction mixture, organic layer is separated and concentrated to isolate the product.

Step 3

Step 3 is a step for obtaining the compound (1) by eliminating the protective group of the compound of the formula (4).

The step can be carried out by contacting the compound (4) with deblocking agent and conventional methods can be applied.

When the protective group for the phenol group is alkyl group having 1 to 6 carbon atoms, examples of the deblocking agent include hydrobromic acid, boron tribromide, and the like, and hydrobromic acid is preferred in view of the cost and handling. The amount of hydrobromic acid is generally 2 to 10 mols, preferably 3 to 7 mols per 1 mol of the compound (4) in view of the yield and the effect corresponding to the amount.

Examples of the solvent include acetic acid, but the solvent is not always required and hydrobromic acid can be used as a solvent.

The amount of the solvent is generally between 200 ml and 1 liter, preferably between 200 and 500 ml per 1 mol of the compound (4).

The reaction temperature is generally in the range from 20 to 150° C., preferably from 50 to 120° C.

As an after treatment, for example, the reaction mixture is poured into water and converted to alkaline, followed by extraction with organic solvent and concentration of the extract to isolate the product.

When the protective group for the phenol group is the trialkylsilyl group having 3 to 18 carbon atoms, fluorides such as hydrogen fluoride, potassium fluoride,, tetrabutylammonium fluoride, and the like; or mineral acids such as hydrochloric acid, hydrogen bromide, and the like can be used for the elimination of the protective group. Hydrochloric acid is preferred in view of the safety and economics.

The amount of the fluoride or mineral acid used is generally 0.01 to 2 mols per 1 mol of the compound (4).

When the protective group for the phenol group is 2-tetrahydropyranyl group, mineral acid is used as a deblocking agent and examples thereof include hydrochloric acid, and the like. The amount of the mineral acid used is generally from 0.001 to 1 mol per 1 mol of the compound (4). As an after treatment, for example, the reaction mixture is poured into water or extracted with hydrochloric acid to form aqueous solution, which is converted to alkaline, followed by extraction with organic solvent and concentration of the extract to isolate the product.

When the protective group for the phenol group is the benzyl group optionally substituted, deblocking of the protective group can be performed by the similar method to one with alkyl protective group having 1 to 6 carbon atoms for the phenol group.

Alternatively, the elimination of the protective group of the compound (4) can be carried out by reduction in the presence of reduction catalyst such as palladium catalyst, and the like. Examples of the palladium catalyst include palladium on carbon, palladium hydroxide on carbon, palladium chloride, palladium black, and the like. Palladium on carbon is preferred in view of the safety and economics.

The elimination of the protective group of the compound (4) can also be carried out according to the conventional methods. For example, when the protective group is alkyl group having 1 to 6 carbon atoms, a method described in Green and Wuts, "Protective Groups in Organic Syntheses, Third Edition" (Wiley International), p 249-257 and p 265-266, respectively, can be used. When the protective group is tetrahydropyranyl, the method described in ibid, p 261 can be used, while when it is trialkylsilyl group, the method in ibid, p 273-276 can be used.

Tolterodine can be optically separated, for example, by using an optically active acid compound (e.g. L-tartaric acid, etc.).

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by way of examples, which are not construed to limit the scope of the present invention.

REFERENCE EXAMPLE 1

Production of 2-benyl-4-methylanisole

A mixture of 4-methylanisole (200 g, 1.64 mol), benzyl alcohol (40.0 g, 0.37 mol) and p-toluenesulfonic acid monohydrate (8.0 g, 0.042 mol) was stirred at 160 to 175° C. for two hours while eliminating water generated by the reaction. After excess 4-methylanisole was distilled off under reduced pressure (inner temperature, 132° C./25 mmHg (3.3 kPa), the residue was dissolved in toluene (50 ml) and then the organic layer was successively washed with water (20 ml), 10% aqueous caustic soda (20 ml) and water (20 ml). After the washed organic layer was concentrated, the residue was distilled under reduced pressure to collect a component fractionated at boiling point of 120-138° C. at 0.7 mmHg (0.09 kPa) as a main fraction (52.75 g, 67.2%). The component was analyzed by NMR to identify 2.7:1 mixture of 2-benzyl-4-methylanisole and 3-benzyl-4-methylanisole.

EXAMPLE 1

Production Of N,N-diisopropyl-3-(2-methoxy-5-methylphenyl)-3-phenylpropanamine

A mixture of 2-benzyl-4-methylanisole and 3-benzyl-4-methylanisole (2.7:1 mixture, 10.0 g, 47.1 mmol) was dissolved in tetrahydrofuran (THF) (300 ml ) under argon atmosphere and cooled to −78° C. To the solution was added dropwise 13% n-butyllithium (34.8 g, 70.7 mmol). After the addition, the mixture was allowed to warm to 0° C., and then stirred for six hours at the temperature. The mixture was cooled again to −78° C., to which 2-(diisopropylamino)ethyl chloride (11.6 g, 70.9 mmol) was added dropwise. The mixture was allowed to warm to the room temperature and then stirred for two hours at room temperature. After adding warm (20 ml), toluene (100 ml) was added thereto. The mixture was phase separated and the organic layer was extracted twice with 10% hydrochloric acid (200 ml). The aqueous layers were combined and, sodium hydroxide (31 g) was added to the combined aqueous layer and then the added mixture was extracted twice with toluene (300 ml and 200 ml, respectively). The organic layers were combined, washed with 5% aqueous sodium chloride, dried over anhydrous magnesium sulfate and then concentrated to obtain 14.65 g of concentrate. The concentrate obtained was added to xylene (120 ml), which was concentrated. This process was repeated three times to yield 12.5 g of the residue. The residue was analyzed by NMR to identify about 10:1 mixture of N,N-diisopropyl-3-(2-methoxy-5-methylphenyl)-3-pheylpropanamine and N,N-diisopropyl-3-(5-methoxy-2-methylphenyl)-3-phenylpropanamine. Yield of N,N-diisopropyl-3-(2-methoxy-5-methylphenyl)-3-phenylpropanamine was 98.5% based on 2-benzyl-4-methylanisole.

$^1$H NMR Data of N,N-diisopropyl-3-(2-methoxy-5-methylphenyl)-3-phenylpropanamine $^1$H NMR (400 MHz, CDCl$_3$);d=0.93 (d, J=1.2 Hz, 6 H), 0.92 (d, J=1.2 Hz, 6 H), 2.09-2,15 (m, 2 H), 2.25 (s, 3 H) 2.32-2.35 (m, 2 H), 2.94-3.00 (m, 2 H), 3.73 (s, 3 H), 4.34 (t, J=7.6 Hz, 1 H), 6.70 (d, J=12 Hz, 1 H), 6.92 (d, J=8 Hz, 1 H), 7.05 (br, 1 H), 7.10-7.18 (m, 2 H), 7.21-7.28 (m, 3 H)

EXAMPLE 2

Production Of N,N-diisopropyl-3-(2-methoxy-5-methylphenyl)-3-phenylpropanamine

A mixture of 2-benzyl-4-methylanisole and 3-benzyl-4-methylanisole (2.7:1 mixture, 10.0 g, 47.1 mmol) was dissolved in tetrahydrofuran (THF) (300 ml) under argon atmosphere and cooled to −78° C. To the solution was added dropwise 13.9% n-butyllithium (32.46 g, 70.5 mmol). After the addition, the mixture was allowed to warm to 0° C., and then stirred for four hours at the temperature. The mixture was cooled again to −78° C., to which 2-(diisopropylamine) ethyl chloride (11.6 g, 70.9 mmol) was added dropwise. The mixture was allowed to warm to the room temperature and then stirred for two hours at room temperature. After addition of water (20 ml), the mixture was extracted twice with 10% hydrochloric acid (25 ml and 15 ml, respectively). The aqueous layers were combined, to which sodium hydroxide (4.9 g) was added and the mixture was extracted twice with toluene (30 ml and 20 ml, respectively). The organic layers were combined, washed twice with 5% aqueous sodium chloride (15 ml), dried over anhydrous magnesium sulfate and then concentrated. To the concentrate of the reaction mixture obtained, xylene (100 ml) was added and then concentrated. The operations were repeated three times to yield 13.7 g of the residue. The residue was analyzed by NMR to identify about 10:1 mixture of N,N-diisopropyl-3-(2-methoxyl-5-methylphenyl)-3-phenylpropanamine and N,N-diisopropyl-3-(5-methoxy-2-methylphenyl)-3-phenylpropanamine. Yield of N,N-diisopropyl-3-(2-methoxyl-5-methylphenyl)-3-phenylpropanamine was 100% based on 2-benzyl-4-methylanisole.

EXAMPLE 3

Production Of Tolterodine

About 10:1 mixture of

N,N-diisopropyl-3(2-methoxy-5-methylphenyl)-3-phenylpropanamine and N,N-diisopropyl-3-(5-methoxy-2-methylphenyl)-3-phenylpropanamine (11.0 g, 32.4 mmol) was dissolved in acetic acid (15 ml). After addition of 47% aqueous hydrobromic acid (25 ml), the mixture was heated to reflux for three hours (bath temperature, 120° C.). The reaction mixture was cooled to the room temperature. After the solvent was distilled off, water (120 ml) and toluene (110 ml) were added to the residue, to which sodium hydroxide (2.2 g) and sodium carbonate (26 g) were added to adjust pH to 11. After the aqueous layer was phase-separated to remove, the organic layer was washed with an aqueous sodium chloride and dried over anhydrous magnesium sulfate. The solvent in the dried solution was distilled off under reduced pressure to obtain 9.04 g of racemic tolterodine (yield 85.7%).

The residue was analyzed by NMR to identify about 10:1 mixture of tolterodine and N,N-diisopropyl-3-(5-hydroxy-2-methylphenyl)-3-pheylpropanamine.

$^1$H NMR of Tolterodine $^1$H NMR (400 MHz, CDCl$_3$); d=1.06 (d, J=6.8 Hz, 6 H), 1.11 (d, J=6.8 Hz, 6 H), 2.11 (s, 3 H) 2.03-2.15 (m, 1 H), 2.24-2.42 (m, 1 H), 2.69-2.73 (m, 1 H), 3.17-3.25 (m 2 H), 4.48 (dd, J=3.6, 11.6 Hz, 1 H), 6.54 (br, 1 H), 6.77 (dd, J=2, 7.6 Hz, 1 H), 7.13-7.27 (m, 1 H), 7.29-7.35 (m, 4 H).

REFERENCE EXAMPLE 2

Production Of Tartaric Acid Salt Of Optically Active Tolterodine

About 10:1 mixture of tolterodine and

N,N-diisopropyl-3-(5-hydroxy-2-methylphenyl)-3-phenylpropanamine (4.0 g, 11.3 mmole) was dissolved in ethanol (10 ml). The solution was heated to 40° C., and then L-tartaric acid (2.55 g, 17.0 mmol) in ethanol (20 ml) was added dropwise thereto. The solution was heated to reflux for one hour and then cooled to 0° C. to precipitate crystals, which were collected by filtration. The crystals were washed with ethanol (3 ml) to obtain 2.33 g of the title compound. Yield of the tartaric acid salt of optically active tolterodine was 43.9% based on the racemic tolterodine.

$^1$H NMR (400 MHz, DMSO-d$_6$); d=1.02-1.07 (m, 12 H), 2.16 (s, 3 H), 2.25-2.26 (m, 2 H), 2.66 (br, 2 H), 3.37-3.43

(m, 2 H), 4.00 (s, 2 H), 4.48 (t, J=8 Hz, 1 H), 6.65 (d, J=8.4 Hz, 1 H), 6.79 (d, J=8.4 Hz, 1 H), 6.99 (s, 1 H), 7.13-7.16 (m, 1 H), 7.24-7.31 (m, 4 H)

The present invention enables a manufacture of tolterodine or salt by less number of steps and industrial scale.

The process according to the present invention can produce tolterodine or its intermediate industrially advantageously with smaller number of steps than the conventional process.

Japanese Patent Application No. 2004-350942 filed on Dec. 3, 2004 is a corresponding Japanese Patent Application on which this nonprovisional application is based, the entire contents of which are hereby incorporated by reference.

What is claimed is:

1. A process for producing tolterodine of the formula (1) or its salt;

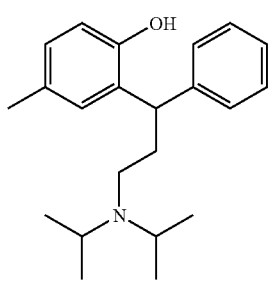
(1)

which comprises a step of reacting a compound of the formula (2)

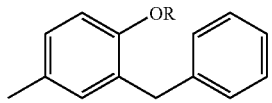
(2)

wherein R represents a protective group of phenol group, with a base to obtain a reaction product, a step of reacting the reaction product with a compound of the formula (3)

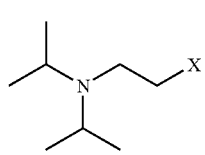
(3)

wherein X represents a halogen atom, alkylsulfonyloxy group or arylsulfonyloxy group, to obtain a compound of the formula (4)

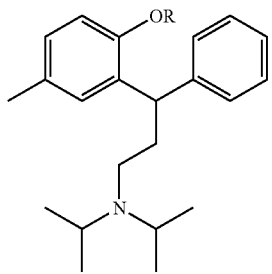
(4)

wherein R has the same meaning as defined above, and a step of eliminating the protective group from the compound of the formula (4).

2. The process according to claim 1, wherein the base is alkyl metal, metal dialkylamide or metal hydride.

3. The process according to claim 2, wherein the base is alkyl lithium or lithium dialkylamide.

4. The process according to claim 3, wherein the base is n-butyllithium, sec-butyllithium, tert-butyllithium or lithium diisopropylamide.

5. The process according to claim 4, wherein the base is n-butyllithium or sec-butyllithium.

6. The process according to claim 1, wherein X in the compound of the formula (3) is chlorine atom, bromine atom, methanesulfonyloxy group, toluenesulfonyloxy group or benzenesulfonyloxy group.

7. The process according to claim 6, wherein X in the compound of the formula (3) is chlorine atom.

8. The process according to claim 1, wherein R is alkyl group having 1 to 6 carbon atoms, benzyl group optionally substituted, trialkylsilyl group having 3 to 18 carbon atoms or 2-tetrahydropyranyl group.

9. The process according to claim 8, wherein R is methyl group, benzyl group, trimethylsilyl group, di-tert-butylmethylsilyl group, tert-butyldimethylsilyl group or 2-tetrahydropyranyl group.

10. The process according to claim 1, wherein the elimination of the protective group from the compound of the formula (4) is carried out by contacting the compound (4) with a deblocking agent.

11. The process according to claim 10, wherein R is alkyl group having 1 to 6 carbon atoms or benzyl group optionally substituted and the deblocking agent is hydrobromic acid or boron tribromide; R is trialkylsilyl group having 3 to 18 carbon atoms and the deblocking agent is fluoride or mineral acid; or R is 2-tetrahydropyranyl group and the deblocking agent is mineral acid.

12. The process according to claim 1, wherein R is benzyl group optionally substituted and the elimination of R is carried out by hydrogenation of the compound of the formula (4) in the presence of a reduction catalyst.

13. A process for producing a compound of formula (4)

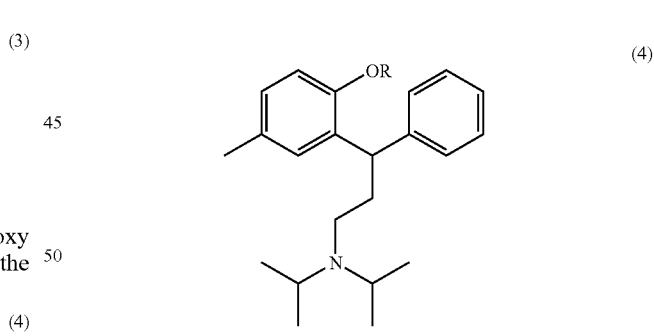
(4)

wherein R represents a protective group of phenol group, which comprises a step of reacting a compound of the formula (2)

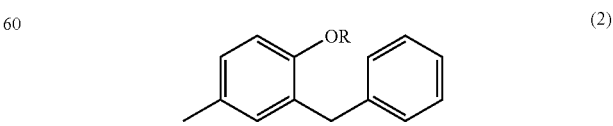
(2)

wherein R has the same meaning as defined above, with a base to obtain a reaction product, and a step of reacting the reaction product with a compound of the formula (3)

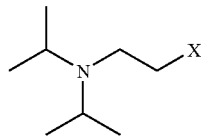

(3)

wherein X represents a halogen atom, alkylsulfonyloxy group or arylsulfonyloxy group.

14. The process according to claim 13, wherein the base is alkyl metal, metal dialkylamide or metal hydride.

15. The process according to claim 14, wherein the base is alkyl lithium or lithium dialkylamide.

16. The process according to claim 15, wherein the base is n-butyllithium, sec-butyllithium, tert-butyllithium or lithium diisopropylamide.

17. The process according to claim 16, wherein the base is n-butyllithium or sec-butyllithium.

18. The process according to claim 13, wherein X in the compound of the formula (3) is chlorine atom, bromine atom, methanesulfonyloxy group, toluenesulfonyloxy group or benzenesulfonyloxy group.

19. The process according to claim 18, wherein X in the compound of the formula (3) is chlorine atom.

20. The process according to claim 13, wherein R is alkyl group having 1 to 6 carbon atoms, benzyl group optionally substituted, trialkylsilyl group having 3 to 18 carbon atoms or 2-tetrahydropyranyl group.

21. The process according to claim 20, wherein R is methyl group, benzyl group, trimethylsilyl group, di-tert-butylmethylsilyl group, tert-butyldimethylsilyl group or 2-tetrahydropyranyl group.

* * * * *